United States Patent [19]
Taylor et al.

[11] Patent Number: 5,244,718
[45] Date of Patent: Sep. 14, 1993

[54] SYNTHETIC FABRICS AND SURGICAL/MEDICAL PRODUCTS MADE THEREFROM

[76] Inventors: Jeffrey L. Taylor, 316 Wilmuth Ave., Cincinnati, Ohio 45215; John M. Smith, 2600 Weymouth Pl.; C. Dean Goad, 2806 Rockwood Rd., both of Greensboro, N.C. 27408

[21] Appl. No.: 860,315

[22] Filed: Mar. 30, 1992

Related U.S. Application Data

[63] Continuation-in-part of Ser. No. 679,775, Apr. 3, 1991, abandoned.

[51] Int. Cl.⁵ .............................................. D03D 3/00
[52] U.S. Cl. .................. 428/229; 139/420 A; 139/420 R; 139/426 TW; 206/440; 229/87.01; 428/225; 428/257; 428/258; 428/259

[58] Field of Search ............... 428/225, 229, 257, 258, 428/259, 265; 206/438, 440; 229/87.01; 139/420 R, 420 A, 426 TW; 2/DIG. 7

[56] References Cited

U.S. PATENT DOCUMENTS

| | | | |
|---|---|---|---|
| 4,461,802 | 7/1984 | Lausch | 428/229 |
| 4,692,365 | 9/1987 | Kratzsch et al. | 428/229 |
| 4,761,321 | 8/1988 | McCall et al. | 428/229 |
| 4,822,667 | 4/1989 | Goad et al. | 428/225 |

*Primary Examiner*—James J. Bell
*Attorney, Agent, or Firm*—Kinney & Schenk

[57] ABSTRACT

A polyester wrapper fabric having permeability for penetration of steam in sterilization surgical instruments. The fabric is a two by two twill in which the filling yarns are core and affect texturized yarn. A herringbone weave is another embodiment. In other embodiments plain woven portions are combined with the twill and herringbone weaves to minimize ravelling.

50 Claims, 3 Drawing Sheets

SYNTHETIC FABRICS AND SURGICAL/MEDICAL PRODUCTS MADE THEREFROM

The present application is a continuation-in-part application of application Ser. No. 679,775, filed Apr. 3, 1991 now abandoned.

The present invention relates to improvements in synthetic fabrics and more particularly to a synthetic fabric intended for use in medical/surgical applications.

Although not necessarily so limited in its broader aspects, the present invention is directed to an improved synthetic wrapper fabric. As the name implies, wrapper fabrics are, primarily, intended for use in forming wrappers. The wrapper may be, simply, a length of the fabric which is peripherally edge bound to prevent fraying. Wrappers, for example, may be folded about a set of surgical instruments to form a package. This package is then sterilized. After sterilization, the wrapped instrument package may be handled, as the need arises, for storage and ultimate delivery to and use by a surgeon in the performance of a surgical procedure. This protocol of handling instruments employed in surgical procedures gives assurance that they will be sterile at the time a surgical procedure is performed.

Traditionally, the medical community has employed cotton muslin as the fabric for such wrappers. The muslin fabric was found to be highly effective in providing the necessary permeability to permit steam, or other sterilization medium, to readily penetrate through to the instruments, packaged therein. Such penetration is required first to effect sterilization, and further to minimize sterilization times, as well as heat and pressure requirements. The same protocol is used to deliver sterilized surgical gowns and other items for use in a surgical procedure.

After sterilization, the packages may be stored and then delivered to an operating room. The wrapper provides protection for the sterilized items during storage and handling and may be removed to provide access to those items, in accordance with accepted protocols, which assure that they are uncontaminated when placed in use.

Such muslin wrapper fabrics were generally formed of plain woven, cotton, spun yarns. With the advent of synthetic yarns, the wrapper fabrics were also formed of spun cotton and synthetic staples, such as polyester. Muslin wrappers have a serious drawback in that they create lint, as the staple fibers separate therefrom in use. Such lint can be a pollutant in the sterilized environment of a surgical arena.

A further short coming of such prior wrapper materials was their relatively short wear life. This to is say that repeated washing and subsequent sterilizations of the wrappers, result in a loss of strength, such that the wrappers could no longer be used for their intended function.

With the advent of continuous filament, synthetic fiber yarns, there were various proposals to use synthetic wrapper fabrics. These proposals have, for the most part, involved the use of polyester yarns. Reference will be made herein to polyester, with the understanding that there are other polymers, such as nylon, which could have equivalent properties.

These continuous filament polyester yarn fabrics possess several advantages over spun yarn fabrics formed of natural and/or synthetic fibers. The staple fibers of spun yarn fabrics tend to separate in use. This produces linting and/or pilling, which becomes a contaminant in the sterile atmosphere sought to be maintained in an operating room. Further, separating of fibers results in a loss of the structure of the fabric to the end that, over time, it looses its structural integrity.

At this point it will be noted that the present invention is directed to fabrics, which are intended for incorporation in reusable items, such as wrappers and surgical drapes, which are reusable. Thus, after each use the fabric is washed, dried and sterilized. These procedures involve the use of harsh detergents, repeated flexing as the fabric is tumbled, both in washing and drying and high temperatures, both in drying and sterilization.

Thus fabrics employed in this medical/surgical environment are subject to much more rigorous conditions, which tend to wear out the fabric, than are found in the more widespread use of fabrics for clothing.

Spun yarn fabrics, particularly those employed for wrappers, or the like, generally speaking, become unusable after 35–40 washing/sterilization cycles.

Continuous filament polyester yarn, wrapper fabrics overcome the noted linting/pilling problems and are highly desirable in that they are durable. That is, these fabrics can be subjected to upwards of 100 washing/sterilization cycles without loosing their structural integrity.

Polyester yarn fabrics also have another characteristic which is desirable in a surgical wrapper. Specifically, the polyester material is hydrophobic and thus non-absorbent. While this hydrophobicity does not provide the further desired characteristic of water repellency, polyester yarns may be treated by known chemicals to provide water repellency. It will be noted that a water repellant fabric resists water penetration where there is little or no hydraulic pressure tending to force the water (and other liquids) through the fabric.

Desirably, a surgical wrapper is water repellant to give further assurance that the sterilized condition of surgical items will be preserved during handling and storage.

Continuous filament polyester yarns were originally comprised of a plurality of essentially straight filaments. Fabrics formed of these yarns were unsuitable for use as a surgical wrapper because of several characteristics. These characteristics are generally referenced as the "hand" of a fabric. "Hand" is a widely used, and accepted term in the textile field, despite the fact that it is highly subjective. While there have been some recent attempts to standardize and quantify the definition of "hand", the accepted practice is for a person to feel and handle a given fabric and then to characterize it in relative terms of flexibility, drapability, surface texture, weight and similar factors.

"Hand", in some respects, reflects aesthetic values. This is to say that a traditionally employed spun yarn or muslin fabric may find preference in the market place simply because it possesses some non-quantifiable characteristic of "hand" which distinguishes it from another fabric, such as a synthetic yarn fabric, which is functionally equivalent.

There are, however, factors of "hand" that do affect the end use of a fabric. For example, continuous filament polyester yarns have a "hand" which has a "slick" feel, compared to cotton muslin. Though not quantified, the continuous filament polyester yarn fabric has a significantly lower coefficient of friction than the "rough" surface of cotton muslin. Continuous filament, polyester yarn wrappers, because of this characteristic, present a serious problem in that when sterilized packages are stacked, in conventional fashion, the packages can slip with respect to each other and topple from the stack.

Another pertinent factor of "hand" is fabric flexibility, which also can be referenced as its ability to drape and conform to a supporting surface. Continuous filament polyester yarn fabrics, at least on a comparable fabric weight basis, generally have less drapability, making more difficult the folding of wrappers to form a wrapped package.

There is a further characteristic of hand which is of significance primarily in synthetic yarn fabrics. This factor is referenced as "memory", or limpness. The "hand" of a muslin fabric is limp and it has no "memory". Thus, when a muslin wrapper is folded to wrap a package of surgical instruments, the folds remain, as formed, and there is no tendency of the wrapper to come loose from the package. A continuous filament polyester yarn fabric wrapper, however, due to the "memory" characteristic tends to unfold, to the end that the wrapper will not properly contain the surgical instruments.

"Hand" as herein used includes the functional characteristics discussed, as well as other characteristics, as would be recognized in the textile art. As will be further noted, the point of reference will be the "hand" of cotton muslin.

The deficiencies of continuous filament polyester yarns in providing a "hand" or feel comparable to spun yarn fabrics led to the developed of what are known as texturized yarns. Texturized synthetic yarns, and polyester yarns in particular, can take many forms. They are generally characterized in that they comprise a plurality of individual filaments, which have been formed in a non-linear, or curvilinear fashion, by various processes. The recognized characteristic of texturized yarns is that they provide fabrics which more closely approximate the hand of fabrics constructed of spun yarns.

The first polyester surgical wrappers known to have any substantial measure of commercial acceptance were formed of texturized polyester yarns, which were substituted for the spun yarns of the plain woven (one by one) muslin fabric. More specifically the referenced wrapper fabric comprised false twist texturized yarns and air texturized filling yarns. One source of these polyester surgical wrappers was Standard Textile Company Inc., Cincinnati, Ohio. Such wrappers and the fabric therefor were identified by the trademark Wrappel.

The texturized polyester yarn fabrics provided significant improvements in "hand" and approached the "hand" of cotton muslin wrapper fabrics. This was true particularly at the time the fabric was manufactured. However, it was discovered that the desired "hand" characteristics progressively degraded as wrappers were subject to repeated washing/sterilization cycles. For example, the surface of the wrappers initially had the desired "roughness" characteristic. However, after as few as 25 washing/sterilization cycles, the surface would become slick and there would be toppling of packages stacked for storage.

While attention has been directed to the problems related to fabrics employed in surgical wrappers, the same fabric can be, and is, used for other purposes in the surgical/medical field as a substitute for cotton muslin. Thus polyester fabric can be employed as a substitute for muslin in surgical drapes to obtain such benefits as the elimination of linting. When so used, it is likewise desirable, if not essential, that the polyester fabric have the same "hand" as cotton muslin, and that such hand be maintained as long as possible when the surgical drape is subject to repeated washing/sterilization cycles.

Accordingly, it is a broad object of the present invention is to provide an improved synthetic yarn fabric which has a "hand" which closely approximates, if not being the same as, the "hand" of cotton muslin.

Another and related object of the present invention is to provide a synthetic yarn fabric which fulfills the foregoing end and which, further, maintains such improved "hand" after repeated washing/sterilization cycles.

A further object of the present invention is to provide reusable, surgical/medical products which have an extended useful life.

In accordance with one aspect of the present ends may be attained by fabric capable of being incorporated in reusable medical/surgical products, which are to be washed, dried and sterilized subsequent to each use. This fabric being characterized in that it has a "hand" which, at least, closely approximates the "hand" of cotton muslin, and is further characterized in that the "hand" of the fabric is not substantially degraded subsequent to a at least 75 washing/drying/sterilization cycles. The fabric of the present invention is further characterized in that it has a vapor permeability sufficient to permit effective penetration by mediums employed in sterilization processes.

The fabric is a tightly woven fabric and is constructionally characterized in that one set, of yarns form, either the warp yarns, or the filling yarns, form floats which define a preponderance of at least one surface of the fabric, and the float forming yarns are an air texturized, core and affect texturized, synthetic continuous filament yarn, and the other set of yarns are texturized, continuous filament, synthetic yarns.

In accordance with other aspects of the invention the foregoing ends may be attained by a fabric, adapted for the same purposes, and having "hand" characteristic, approximating cotton muslin, which survive repeated washing, drying, sterilization cycles. This fabric is structurally characterized in that it is a tightly woven fabric and either the warp yarns or the filling yarns consists substantially entirely of core and effect, air texturized, synthetic, continuous filament yarns and other of said warp yarns or filling yarns is formed of continuous, synthetic filament yarns. Further at least one surface of this fabric is formed by a preponderance of the core and effect, air texturized, synthetic, continuous filament yarn.

In accordance with further aspects of the invention, the foregoing ends may be attained by a fabric for the same uses and providing the same "hand" characteristics. This fabric is also a tightly woven fabric and is constructionally characterized in that the fabric is woven with a weave pattern providing raised ribs, and ribs are formed by air texturized, continuous filament synthetic yarns, thereby enhancing the roughness factor of the said fabric's "hand".

Other features of the invention are found in the use of a twill weave pattern for the fabric, with a two by two twill being particularly advantageous. Other unique advantages are found in the use of air texturized, core and effect yarns as the filling yarns, with the air texturized core and effect yarns having a denier substantially greater than that of false twist, texturized yarns employed as warp yarns. Further features of the invention are found in the deniers of the yarns and the end and pick counts of the fabric.

Another feature of the invention is found in a fabric, as above characterized, which is a broken twill weave, also referenced as a herringbone weave.

Yet another object of the present invention is to minimizing ravelling in the type of fabrics above characterized.

More specifically, there is a tendency for the yarns of such fabrics to fray, or ravel, when a length of fabric is cut, as by dies, to form components which are employed as wrappers, or otherwise incorporated into a medical/surgical product.

Such ends are broadly attained by the provision of plain woven portions between the ribs of a twill or herringbone portion.

In accordance with further aspects of the invention, the foregoing ends are attained by surgical/medical product incorporating the fabrics above characterized.

The above and other related objects of the invention will be apparent from a reading of the following description of the invention, with reference to the accompanying drawings and the specific examples set forth, the novelty of which is pointed out in the appended claims.

The present invention, in providing a new and improved fabric, is based on the use of known yarns, which may be woven by existing looms employing conventional operating and processing techniques. To the extent that such conventional techniques have a bearing on the present invention, they will be further described. As will be pointed out, the features of the invention are found in the specific yarns and weaves, which provide a synthetic fabric which approaches, if not being essentially the same as, the "hand" of cotton muslin wrapper fabric. This fabric is further characterized in that this improved "hand" survives repeated washing/sterilization cycles.

Figure 1:
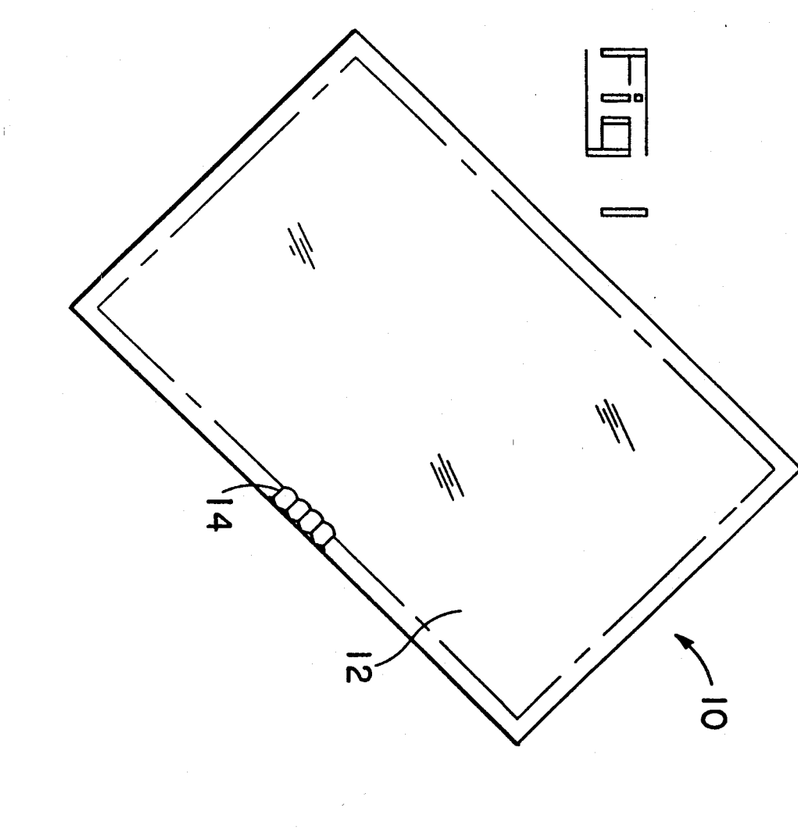
FIG. 1 is a perspective view of a wrapper formed of wrapper fabric of the present invention.

FIG. 1 illustrates a wrapper 10 comprising a length of wrapper fabric 12, which is edge bound, as by overstitching 14. The overstitching extends around the periphery of the wrapper 10 and serves the function of preventing the fabric yarns from ravelling. Any suitable synthetic yarn can be used for the overstitching 14, provided it is compatible with the use to which the wrapper is to be put. Use of a polyester yarn for this purpose is acceptable.

Figure 2:
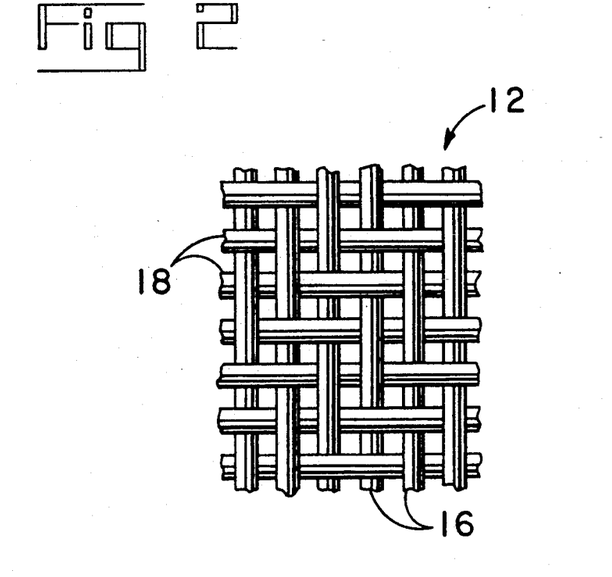
FIG. 2 is a greatly enlarged view of the fabric, illustrating the weave thereof.

The fabric 12 is, preferably, a two-by-two twill weave, as illustrated in FIG. 2. The resultant fabric has a diagonal, ribbed effect, produced by floats, which characterizes twill fabrics. This ribbed effect is also indicated in FIG. 1.

Figure 3:
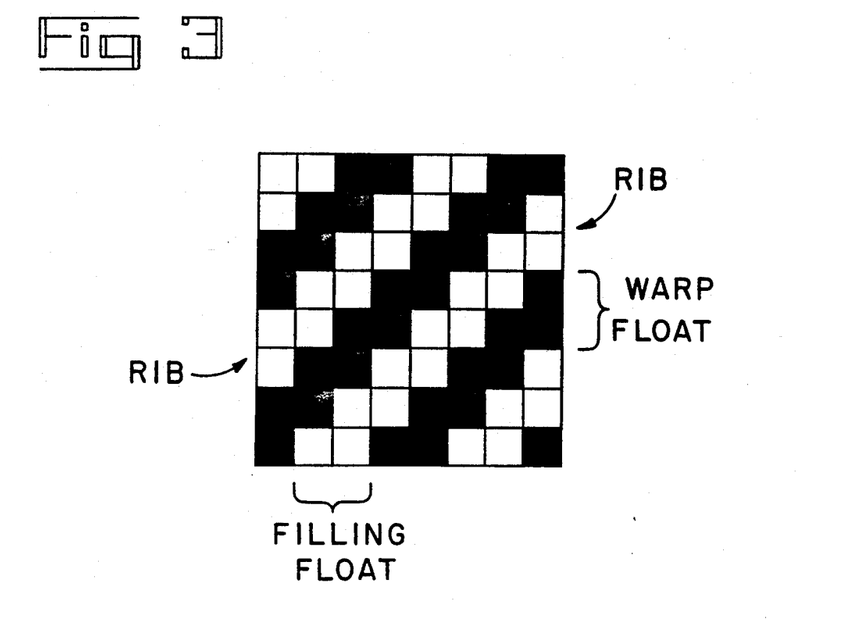
FIG. 3 is a diagrammatical representation of the fabric weave illustrated in FIG. 2.

For purposes of reference hereinafter, reference is made to FIG. 3, which is a diagrammatic representation of the twill weave seen in FIG. 2. In a woven fabric, the surface is defined by either warp yarns or filling yarns, dependent on the weaving pattern. By convention, in a grid, as shown in FIG. 3, the darkened squares represent warp yarns and the white squares represent filling yarns, on the viewed surface of the fabric.

By way of further explanation of the known, two-by-two twill weave, the filling floats, which overlie two warp yarns, are identified by a legend. During the weaving process, a greater tension is applied to the warp yarns. The result is that the filling yarn floats are raised to form angled ribs on the surface of the fabric.

The improved "hand" of the present wrapper fabric is also attributable to the use of core and effect, air texturized, texturized, yarns and, more specifically, polyester, core and effect air texturized, yarns.

In the preferred fabric, the filling yarns 18 are polyester, core and effect air texturized yarn. The warp yarns 16 are a polyester, false twist texturized yarn.

A texturized yarn is one comprising a plurality of synthetic filaments, which are deformed from a linear state to a convoluted or curvilinear state. Texturization increases the bulk of the yarn. Thus, a texturized yarn formed from a yarn of a given denier, after texturization, has an increased denier, referenced as the bulked denier. The above referenced false twist texturized yarn is one of many forms of texturized yarns.

Core and effect, air texturized yarn is a specialized form of texturized yarn characterized by two or more sets, or plies, of filaments. Briefly, there is a core set of filaments which is surrounded by a second set of filaments, which may be coiled or looped thereabout. The first set of filaments, i.e. the core, may be essentially straight, or may be texturized (increased in bulk) to a relatively limited extent. The second, or "effect" set, of filaments is texturized to substantially increase its bulk. As this is done, filament loops are formed which contribute to the improved "hand" which is obtained from fabrics constructed therefrom. Polyester core and effect, air texturized yarn, as herein preferred is commercially available from various manufacturers.

These texturized yarns increase the bulk of the filaments and are recognized as providing fabrics, knit or woven therefrom, with a "hand", which to one degree or another, resembles the "hand" of corresponding fabrics formed of spun yarns.

Both false twist texturized yarns and core and effect, air texturized yarns may be thermally set to provide relative dimensional stability. The yarns 16 and 18 are both, preferably set yarns.

Generally speaking, core and effect air texturized yarns are more expensive than comparable false twist texturized yarns.

Both the warp yarns 16 and filling yarns 18 may be formed of core and effect, texturized yarns. When this is done the resultant fabric more closely approximates the "hand" of cotton muslin wrapper fabrics. However, when only one of the yarns is core and effect air texturized yarn, the "hand" of cotton muslin is sufficiently approximated for most purposes. Thus, for reasons of economy, it is preferred to employ core and effect air texturized yarn for only one or the other of the warp or filling yarns. It is further preferred to employ false twist yarns as the warp yarns and core and effect yarns as the filling yarns. This preference is predicated on the fact that the false twist yarns are more uniform in quality and are, thus, best employed as warp yarns.

The preferred two by two twill fabric of the present invention is further characterized in that the core and effect, air texturized, polyester filling yarns 18 have a denier substantially greater than, and preferably about twice, the weight of the false twist texturized, warp yarns 16. The preferred bulked denier of the filling yarns is approximately 170 and the preferred bulked denier of the warp yarns is approximately 78.

This preferred fabric is further characterized by a weave construction which comprises approximately 145 ends per inch and 105 picks per inch. These pick and end counts are based on a finished fabric and can vary from the pick and end counts of the "as woven" fabric, as will be later discussed.

The preferred fabric has a textile (as woven), or yarn, weight of approximately 3.6 ounces per square yard. Subsequent to weaving, various finishes are applied to fabric to provide properties required, or desired, for its use in surgical wrappers and other medical/surgical products. This finishes may include dyes, antimicrobial agents, burn rate retardants, and water repellant finishes.

These finishes may be applied using known compounds and existing procedures, to obtain the desired characteristics. After application of these finishes the weight of the preferred fabric may increase to as much as four ounces per square yard.

As was previously indicated, the present fabric may be woven on conventional looms and subsequently processed in a accordance with known techniques. The referenced finish treatments are applied during this subsequent processing. For a fuller understanding of the invention, a typical procedure for manufacturing the preferred fabric will now be described.

The present fabric would thus be woven in a standard two by two twill pattern. The woven fabric would then be cleaned, i.e., scoured, to remove lubricants and the like that are added to the fabric in the weaving process. In this cleaning process, there will be some shrinking of the fabric.

After cleaning, the fabric is dried and heat set to a final dimension. In the drying/heat setting process the fabric may be positively stretched or negatively stretched (shrunk) to establish the end and pick counts of the finished fabric. By employing negative stretch it is possible to provide a greater number of end and pick counts than can be provided by a given loom. In any event, when referencing end and pick end counts herein, it is the final form of the fabric that is intended, not its "as woven" condition.

The finish treatments may be applied in either a batch process or a continuous process, all as is well known in the art. It is to be understood that as much as 10% of the weight of the wrapper fabric of the present invention may be comprised by these finish treatments.

The preferred fabric, when ready for use, with or without the application of such finishes, possesses a "hand" which is essentially the same as the "hand" of a cotton muslin fabric.

In particular, the "hand" of the present fabric is superior to that of the above referenced, wrapper fabric which was a plain woven fabric (one by one) wherein the warp yarns were false twist, polyester, set yarns and the filling yarns were air texturized, set yarns (note, "air texturized" yarns are structurally distinguished from "core and effect, air texturized yarns, in that they are a single ply yarn). The "hand" of that prior art fabric is readily distinguishable from the "hand" of cotton muslin, albeit the difference is sufficiently small for the fabric to enjoy substantial commercial acceptance because of its offsetting advantages.

The superiority of the preferred fabric of the present invention is further demonstrated by its durability. This is to say that the desirable "hand" characteristics survive repeated washing/sterilization of upwards of 100 cycles. In contrast, the desired "hand" characteristics of the referenced prior art fabrics can suffer substantial degradation after as few as 25 washing/sterilization cycles.

As has been previously indicated, the roughness factor of "hand" is of particular significance in providing a relatively high coefficient of friction for surgical wrappers. In addition to the use of core and effect, air texturized, polyester yarns, it is believed that the improvements are attained through the use of the two by two twill weave pattern. The resultant ribbed configuration of the surface of the fabric enhances surface roughness. Further, by employing filling yarns having a denier substantially greater than the denier of the warp yarns, the surfaces of the fabric are predominately defined by air pressurized, core and effect, polyester yarns, thereby taking maximum advantage of the characteristics of that yarn.

The preferred two by two twill fabric, has a further advantage in that it provides an effective bacteria filtration efficiency. Bacteria filtration capability is a requirement for surgical wrappers, going to maintaining the sterility of the items packaged therein, particularly during extended storage. It is known that bacteria filtration efficiency is an inverse function of the size of the pores, or interstices, between the yarns and fibers of a fabric, and the length of the passageways formed thereby, through which bacteria could travel to penetrate the fabric and contaminate items therein.

There is a further requirement for surgical wrappers in that it is desirable that the fabric be readily penetrated by steam, or other sterilizing mediums, to sterilize the items packaged therein. The obvious means for facilitating steam penetration is to provide a fabric having relatively large pores.

The present fabric uniquely provides both of these ends in having a relatively high bacteria filtration efficiency and the capability of being penetrated by steam, as measured by the rate at which air may flow therethrough. Equally important, it is to be remembered, these ends are attained by a polyester fabric, which possesses the desired "hand" characteristics of cotton muslin. Again, it is believed that these unique ends are attributable to the twill weave and the high bulk, high filament, content of the fabric.

The preferred construction of a two by two twill fabric may be modified within the following ranges to provide a fabric having the referenced, improved "hand" characteristics. The denier of the false twist texturized, warp yarns may range between approximately 50 and 150. The denier of the air texturized core and effect filling yarns may range between approximately 100 and 300. The end count may range between about 100 and 200 per inch and the pick count may range between 80 and 120 per inch. The fabric weight preferably ranges between three and five ounces per square yard, with fabric weights between 2 and 10 ounces per square yards being acceptable.

The two by two twill weave is preferred for several reasons, discussed above. However, the broader concepts of the invention are not limited to this specific weave. The two by two weave provides the same surface characteristics on both sides of the fabric. Therefore, the surface characteristics are not "sided". This is of advantage in such uses as a surgical wrapper, where it would be an annoyance, to identify a particular surface to be disposed on the outside of the package. Thus it is preferred that the fabric properties be symmetrically sided. Such end could also be attained by a three by three pattern.

Also there are end uses of the present fabric, where the configuration of the article, such as a surgical drape, dictates which side will be oriented in a position where it will be exposed in use. Thus, if it is desired that surface have a rough feel, or high coefficient of friction, and that the other side have a slicker characteristic, an unbalanced twill weave, such as a two by one or three by one could be employed.

Twill weaves are characterized in that they form floats. Floats are defined as yarns, warp or filling, which span two or more of the opposite set of yarns (warp or filling) of the fabric. Thus, the broad aspects of the invention include forming such floats with core and effect, air texturized, continuous filament polyester yarns.

Thus, the broader aspects of the invention may be further characterized as being in the provision of a fabric having at least one surface which is formed by a preponderance of air texturized, core and effect polyester yarn. As indicated, this end may be attained through the use of twill weaves. Irrespective of weave, this end can also be attained by employing core and effect, air texturized, yarns having a denier substantially greater than the denier of false twist yarns, where one type of yarn is used as the warp yarn and the other type of yarn is used as the filling yarn.

The present fabric may also be provided with a conductive characteristic for the dissipation of static electricity and the prevention of static electricity discharges which could be the source of ignition for explosive atmospheres frequently found in an operating arena. This end is attained through the use of a carbonaceous yarn. More specifically, selected warp yarns are formed by carbonaceous yarns. These carbonaceous yarns are available under the trademark Neg-a-Stat from E. I. duPont.

It has been found that incorporation of approximately 0.9%, on a weight basis, of the Neg-a-Stat yarn, provides the requisite static electricity dissipation property. This end is attained in the present fabric by employing Neg-a-Stat yarns as every 35th warp yarn.

The following example is presented to further exemplify the invention.

EXAMPLE 1

Fabric was woven on a standard air jet loom type loom. The warp yarn (16) was a 1/70/34 false twist texturized set polyester yarn. This yarn had a bulked denier of 78. This yarn was manufactured by Unifi, Inc, Greensboro, N.C. The filling yarn (18) was a 2/70/34 core and effect, air texturized, set polyester yarn having a bulked denier of 170. This yarn was manufactured by Glen Raven, Inc. Glen Raven, N.C.

The set up of the loom provided 129 ends per inch and 98 picks per inch. The fabric was woven with a nominal width of 78 inches. The woven fabric had a greige weight of 3.69 ounces per square yard.

After weaving, the fabric was cleaned by scouring. The fabric was then dyed in a pad bath and heat set under the following conditions:

| Pad Bath Chemicals | Amount by Weight |
| --- | --- |
| Isopropanol (non-rewetting wetter) | 1.0% |
| Acetic Acid (84%) | 1.12% |
| Urea (humectant) | 2.0% |
| Terasil Blue 3RL | 0.5% |
| Terasil Red FB | 0.19 |
| Cyantex 655 (antimigrant) | 2.5% |
| Water | Balance |
| Fabric wet pick-up | 50–60% |
| Oven dwell time | 30 seconds |
| Oven temperature | 410° F. |

After being thus dyed for identification, heat set and washed, the fabric was finished, to provide antimicrobial properties and to enhance its water repellency, in a pad bath under the following conditions:

| Pad Bath Chemicals | Amount by Weight |
| --- | --- |
| Isopropanol (non-rewetting wetter) | 1.0% |
| Dow Corning 5700 (antimicrobial) | 1.0% |
| Zonyl NWG (flourochemical) | 6.25% |
| Water | Balance |
| Fabric wet Pick-up | 50–60% |
| Oven dwell time | 30 seconds |
| Oven temperature | 350° F. |

The following "performance" tests were then performed on samples:

| Test | Result | Target |
| --- | --- | --- |
| Grab Tensile Strength (lbs.) ASTM-1682-64 | | |
| warp | 160 | 140 |
| fill | 160 | 140 |
| Air Permeability (cfm/sq. ft. @ 0.5 in.) ASTM-737-75 (Frazier Test) | 11.0 | 8.0 |
| Hydrostatic pressure (cm.) AATCC-127* | 29 | 25 |
| Spray rating AATCC-22-1980 | 95 | 90 |
| Alcohol Repellency INDA 80.9 | 9 | 7 |
| Oil Repellency INDA 80.8 | 4 | 4 |
| Water Impact AATCC-42-1985 | 0.15 | 0.75 |
| Bioactivity Dow Corning CTM-0923 | 99% kill | 90% kill |
| Linting INDA 160.0-83 | 1,000 particles per 10 minutes | 2,000/ 10 min. |
| Flammability (CS 191-53) | Class I | Class I |

*This is known as a Suter rating. The actual measurement, expressed as a number, is in centimeters of water head to effect penetration of a fabric sample.

Portions of the fabric web were then fabricated into wrappers, as shown in FIG. 1. Similar conventional wrappers of cotton muslin were then used as a basis of comparison for determining the "hand" of the wrapper produced in this example. A panel of individuals performed feel tests of the present wrappers and the conventional muslin wrappers and the referenced prior art, polyester fabric wrappers. The panel members were unable to identify any substantial difference in "hand" between the conventional wrappers and the polyester fabric wrappers and were further able to identify a substantial improvement in hand over the prior art polyester fabric wrappers.

The wrappers of the present invention were then subject to 100 washing/sterilization cycles in two different institutions. Each institution employed a washing/sterilization cycle generally comprising an initial flush in which the wrappers were soaked in water at 90°–100° F. for three to five minutes. The wrappers were then soaked in an alkali (with a ph in excess of 10) bath at 120°–140° F. for three to five minutes to loosen dirt. Next the wrappers were placed in a detergent bath at approximately 160° F. for approximately eight to ten minutes. Next is a bleach bath at approximately 160° F. for approximately five minutes. This is followed by one or more rinsings at temperatures which may be progressively reduced from 140° to ambient temperature. Finally, there is a acid sour bath in which the ph is adjusted to the four to five range, and in which a softening agent may also be employed. There is then one last rinse bath.

The wrappers were mechanically agitated in some, if not all of these baths. Also, following each bath, there was an extraction (spin) cycle to minimize the liquid carried over to the succeeding process.

The fabrics were then dried in a tumbling dryer at an average temperature of 160° F. Typical drying times for wrappers are in the order of 20 to 30 minutes. It is to be noted that there can be hot spots in such dryers, which can subject the wrappers to temperatures in excess of 400° F.

After drying, the wrappers were wrapped about surgical items and then place in an autoclave and the wrappers, and the contents of the packages, which they enclosed, were sterilized by pressurized steam at a temperature of approximately 270° F., four minutes.

The samples were then reexamined by a panel which was unable to determine any substantial degradation of the "hand" of the fabric. The samples were also tested by forming wrapped packages, which were then capable of being stacked, evidencing that the "rough" surface characteristic was sufficient for purpose of preventing toppling of such stacks.

EXAMPLE 2

Fabric was woven and processed in a fashion identical to that of Example 1, employing the same textured warp and fill yarns and the same number of picks and ends. However, as opposed to the two by two twill weave of Example 1, the fabric of Example 2 was a broken twill, two by two weave, also known as a herringbone weave, both weaves being, per se, well known in the art.

The fabric of Example 2 was tested in the same fashion as the fabric of Example 1 and found to have the essentially the same "performance" test characteristics, and other characteristics, as the fabric of Example 1, both before and after being laundered and sterilized for a limited number of cycles.

Further lengths of fabric have been produced employing the same constructions as in Example 1 (twill) and Example 2 (herringbone) varying only in that the number of picks was in the order of 90-92 per inch. The functional characteristics (Suter ratings, permeability, "hand", etc.) of such fabrics were found to be acceptable and fundamentally the same as the fabrics of Examples 1 and 2.

As indicated above a herringbone weave is a well known weaving pattern. It is likewise characterized by a series of staggered floats that form ribs on the surface of a fabric. The herringbone weave is also known as a broken twill weave and is distinguished from a "standard" twill weave in that the floats have a zigzag pattern, being first angled in one direction for a given number of ends and then being angled in the opposite direction for the same number of floats. Subsequent reversal in the direction in which the floats are staggered produce a balanced zigzag pattern of ribs on the surface of the fabric.

Figure 4:
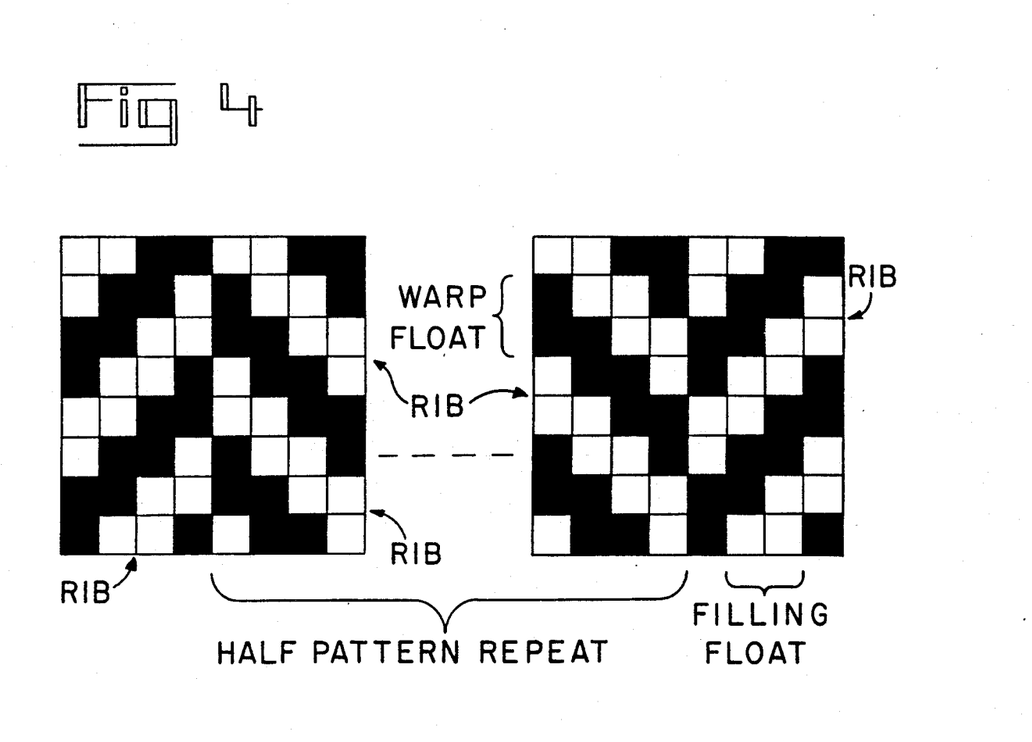
FIG. 4 is a partial, diagrammatic representation of a second fabric embodying the present invention.

The herringbone weave is further illustrated in FIG. 4 by a conventional weaving pattern. Legends depict the warp and filling floats and the ribs defined thereby. The weaving pattern grid is broken away to illustrate that a "half pattern" repeat illustratively comprises 36 ends (warp yarns). With the defined yarns and picks/ends per inch, this produces a band of ribs having a width of approximately ¼ inch. On each side of this band, the half pattern is repeated with the ribs angled in the opposite direction. A full pattern would have a width of approximately ½" and include two warpwise bands, one angled in one direction and the other angled in the opposite direction. This was the construction of the fabric of Example 2.

The preferred half pattern width ranges from ⅛ to ½ inch. It is to be appreciated that the pattern width of the herringbone weave is primarily dictated by aesthetics. This is to say that the preferred range provides an attractive appearance, however patterns having greater width could also be employed.

The variables relating to twills are also applicable to herringbone weaves. A balanced (ribs on both sides of the fabric) two by two, herringbone weave is preferred. The ribs in Example 2 were staggered laterally approximately ¼ inch in forming the herringbone pattern. The degree to which the ribs are laterally staggered in not critical.

The herringbone weave of Example 2 has the advantage of eliminating any directional characteristic from the fabric. This is to say that a twill pattern does have a directional characteristic in that the its parallel ribs are angled in the same direction. This directional characteristic is eliminated by the oppositely angled ribs of the herringbone pattern. Thus, the inter-acting friction forces, between stacked, wrapped packages will not be affected by the relative orientation of wrapped packages.

The herringbone pattern also gives a visual indicia for distinguishing one wrapper fabric from another. This is to say that wrapper fabrics can be used for different purposes. The improved fabric of the present invention can be woven with a plain twill pattern where it is to be used for one purpose and woven in a herringbone pattern, where it is to be used for another purpose.

As has been previously indicated, fabrics of the present invention can also be incorporated in reusable, surgical drapes. Such drapes are an improvement over prior drapes incorporating fabrics previously recognized by those skilled in the art as being suitable to meet the requirements of surgical drapes. These requirements, it is to be noted, are essentially the same as those for surgical wrappers, insofar as "hand" is concerned, with a like need for durability to reduce the per use cost of the drapes.

Figure 5:
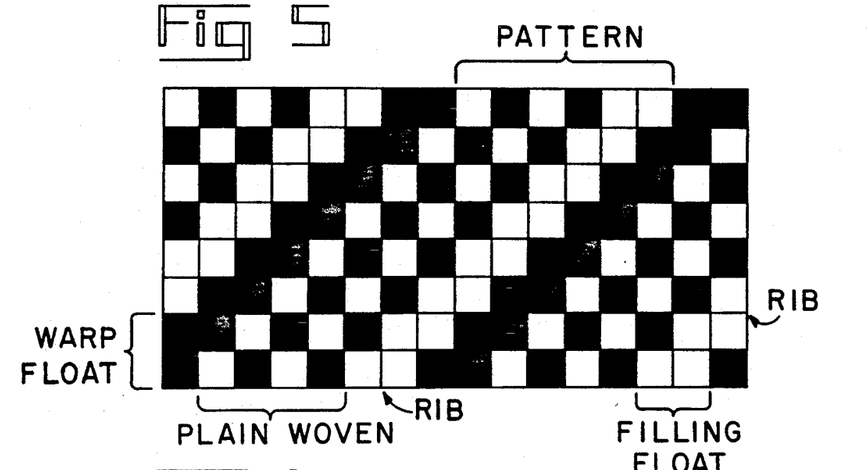
FIG. 5 is a partial, diagrammatic representation of a third fabric embodying the present invention.
Figure 6:
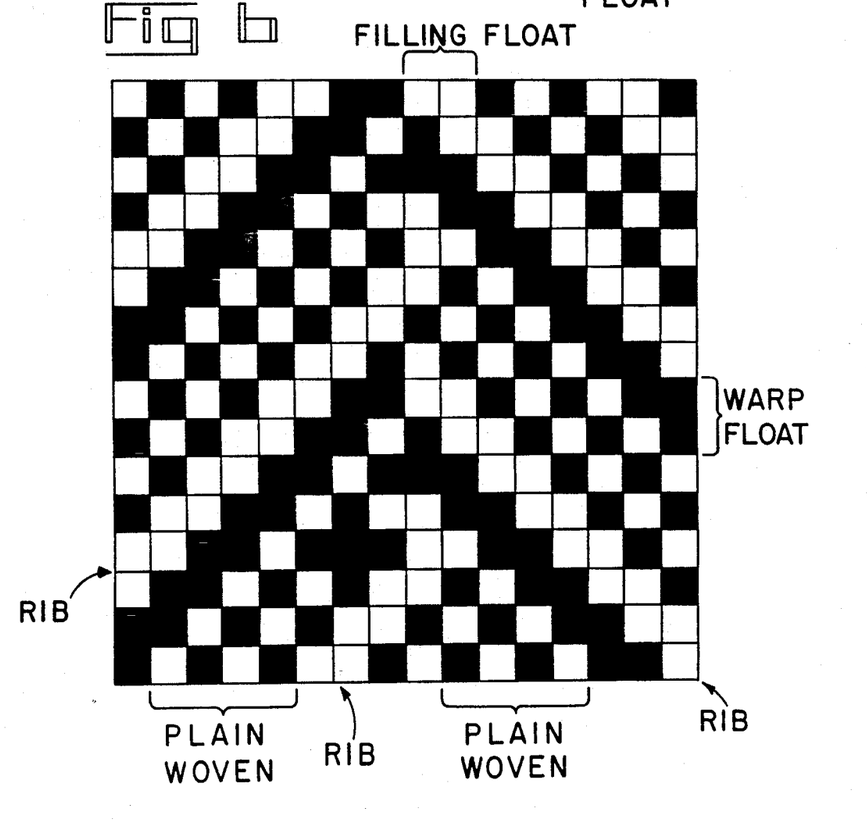
FIG. 6 is a diagrammatic representation of a fourth fabric embodying the present invention.

Reference is next made to FIGS. 5 and 6 for a description of modifications of the fabrics of Example 1 (FIGS. 2, 3) and Example 2 (FIG. 4). The fabrics of FIGS. 5 and 6 introduce plain woven portions between the floats which define the ribs of the Fabric.

The "plain woven" variant of the twill fabric is illustrated in FIG. 5. It can be characterized as a "2/2.1/1.1/1" Right Hand twill. This is to say that the fabric comprises successive (repeated) patterns, each comprising a two by two weave of the warp and filling yarns and then plain woven portion comprising two "1/1 repeats". A "1/1 repeat" comprises a single cross over of a warp yarn and a filling yarn. A "1/1 repeat" should not be confused with a pattern repeat.

The "plain woven" variant of the herringbone fabric is illustrated in FIG. 6. It can be characterized as "2/2.1/1.1/1 RH (right hand).2/2.1/1.1/1 LH (left hand)" herringbone. Due to space limitations, a full pattern repeat is not shown in FIG. 6. Such pattern would be similar to the herringbone construction of FIG. 4, comprising two half pattern repeats (right hand and left hand).

The "plain woven" twill and herringbone fabrics may be woven of the same yarns, processed in the same fashion as described in connection with Examples 1 and 2. Due to the inclusion of "plain woven" portions, the number of picks, in the finished fabric, is limited to approximately 90, with approximately 145 picks.

The "plain woven" fabrics, so constructed, on balance, have at essentially the same desired properties of the corresponding twill and herringbone fabrics described in greater detail in Examples 1 and 2. The desired, frictional characteristics are essentially the same. The "hand" of the fabrics of FIGS. 5 and 6 were a notable improvement over prior art, synthetic wrapper fabrics, but somewhat stiffer, i.e., less drapable, than the fabrics of FIGS. 3 and 4. However, the frictional properties were improved, i.e., the spacing between the ribs was increased by the "plain woven" portions, increasing the effective coefficient of friction. This characteristic increased the effectiveness of wrapper fabric in preventing slippage between stacked, wrapped packages.

The primary benefit of including "plain woven" portions is to minimize ravelling of the fabric. This is to point out that a woven length of fabric must be cut in order to fabricate a surgical wrapper, or other medical/surgical product. It has been found that the twill and herringbone fabrics (of Examples 1 and 2) tend to ravel after being cut into pieces for the fabrication of a medical/surgical product. The tendency to ravel, or fray, requires special care in the handling of the cut pieces as they are incorporated into a medical/surgical product. In particular, ravelling can present problems in stitching fabrics, as in edge binding a fabric piece by overstitching (14) in forming the wrapper 10 seen in FIG. 1. The provision of the "plain woven" portions retards ravelling to an extent for the cut pieces to be handled and sewed without special handling that would involve increased care and greater handling. The end result is that these fabrics can be more economical included in medical/surgical products.

A further advantage of incorporating "plain woven" portions is that it is possible to provide additional visual affects, which can be a further indicia that the product, into which the fabric is incorporated, has a designated purpose or function.

As will be apparent from the above descriptions, the invention, in its broader aspects, comprises a fabric in which at least one surface is defined by floats. Floats are yarns, warp or filling, which pass over two or more yarns, with which the float ares are interwoven. One preferred construction is a twill weave in which both the warp and filling yarns define floats. The herringbone weave is, in a generic sense, a twill weave.

The "plain woven" versions comprise a pattern of rib forming floats and one or more, "1/1 repeats". Preferably two "1/1 repeats" are employed in the "plain woven" portion. The number of "1/1 repeats" in a weave pattern can be greater than two. For most constructions, the upper limit of "1/1 repeats" would be approximately four. For "plain woven" twill this would be expressed as "2/2.1/1.1/1.1/1". The "2/2.1/1.1/1" constructions are preferred in that the provide effective minimization of ravelling and enhancement of the frictional characteristic, while have only a minimal affect on the desired "hand" of the fabric.

The fabric of the present invention has been described in connection with the fabrication of surgical wrappers, as shown in FIG. 1 of the drawings. This surgical wrapper is, itself, unique in that it provides a reusable product which is superior to wrappers which incorporated fabrics, recognized by those skilled in the art, as being suitable for the functions, purposes and requirements of reusable surgical wrappers.

The term medical/surgical products is used to designate the improved products which may be fabricated from the fabric of the present invention.

It is to be appreciated that the spirit and scope of the present invention is to be derived from the following claims.

Having thus described the invention, what is claimed as novel and desired to be secured by Letters Patent of the United States is:

1. A fabric for use in reusable medical/surgical products, which are to be washed, dried and sterilized subsequent to each use,
   said fabric being characterized in that
   it has a "hand" which, at least, closely approximates the "hand" of cotton muslin, and
   further characterized in that
   the "hand" of the fabric is not substantially degraded subsequent to a substantial number of washing/drying/sterilization cycles,
   said fabric being further characterized in that
   it has a vapor permeability sufficient to permit effective penetration by mediums employed in sterilization processes,
   said fabric being a tightly woven fabric and
   constructionally characterized in that
   it is formed by a set of warp yarns and a set of filling yarns, and one set of yarns form floats which define a preponderance of at least one surface of the fabric,
   and further characterized in that
   the yarns forming the floats are an air texturized, core and affect texturized, synthetic continuous filament yarns, and
   the other set of yarns are texturized, continuous filament, synthetic yarns.

2. A fabric as in claim 1
   further characterized in that
   the fabric weave is a twill and
   the filling yarns are an air texturized, core and effect yarn.

3. A fabric as in claim 2
   further characterized in that
   the fabric weave is a broken twill, herringbone weave.

4. A fabric as in claim 2 further characterized in that the warp yarns are false twist texturized yarns.

5. A fabric as in claim 4 further characterized in that the fabric weave is a balanced weave, thereby providing the same characteristics on opposite sides of the fabric.

6. A fabric as in claim 5 further characterized in that the fabric weave is a two by two twill.

7. A fabric as in claim 6 further characterized in that the fabric weave is a broken twill, herringbone weave.

8. A fabric as in claim 6 further characterized in that the warp and filling yarns are polyester yarns.

9. A fabric as in claim 1 further characterized in that the yarns forming the floats have a bulked denier substantially greater than that of the other set of yarns.

10. A fabric as in claim 5 further characterized in that the filling yarns have a bulked denier substantially greater than that of the warp yarns.

11. A fabric as in claim 8 further characterized in that the filling yarns have a bulked denier substantially greater than that of the warp yarns.

12. A fabric as in claim 7 further characterized in that the filling yarns have a bulked denier substantially greater than that of the warp yarns.

13. A fabric as in claim 11 further characterized in that the filling yarns are a two ply, core and effect, air texturized, continuous filament yarn, having a bulked denier approximately twice that of the warp yarns.

14. A fabric as in claim 6 further characterized in that the bulked denier of the filling yarns is between approximately 100 and 300, and the bulked denier of the warp yarns is between approximately 50 and 150.

15. a fabric as in claim 13 further characterized in that the bulked denier of the filling yarns is approximately 170, the bulked denier of the warp yarns is approximately 78, the fabric has between approximately 100 and 200 ends per inch and between approximately 80 and 120 picks per inch, and the weight of the weight of the yarn content of the fabric is between approximately 2 ounces and 10 ounces per square yard.

16. A fabric as in claim 15 further characterized in that there are approximately 145 ends per inch, there are approximately 105 picks per inch, and the weight of the yarn content of the fabric is between approximately 3 and 5 ounces per square yard.

17. A fabric as in claim 16 further characterized in that the filling yarns are 2/70/34 yarns having a bulked denier of 170, and the warp yarns are 70/34 yarns having a bulked denier of 78.

18. A fabric as in claim 13 further characterized in that the fabric weave is a broken twill, herringbone weave.

19. A fabric as in claim 1 further characterized in that the fabric comprises finishes, applied subsequent to weaving, which provide a desired color for the fabric and provide other desired characteristics, and further characterized in that the finishes comprise no more than about 10% of the fabric weight.

20. A fabric as in claim 14 further characterized in that the core and effect, air texturized, yarns and the false twist texturized yarns are heat set, and the fabric is heat set, all to provide dimensional stability for the fabric.

21. A fabric as in claim 8 further characterized in that the fabric comprises evenly distributed carbonaceous yarns, comprising approximately 0.9% of the weight of the fabric.

22. A fabric for use in reusable medical/surgical products, which are to be washed, dried and sterilized subsequent to each use, said fabric being characterized in that it has a "hand" which, at least, closely approximates the "hand" of cotton muslin, and further characterized in that the "hand" of the fabric is not substantially degraded subsequent to a substantial number of washing/drying/sterilization cycles, said fabric being further characterized in that it has a vapor permeability sufficient to permit effective penetration by mediums employed in sterilization processes, said fabric being a tightly woven fabric and constructionally characterized in that comprises warp yarns and filling yarns and at least one of the warp yarns or the filling yarns consists substantially entirely of core and effect, air texturized, synthetic, continuous filament yarns, the other of said warp yarns or filling yarns is formed of continuous, synthetic filament yarns, and at least one surface of said fabric is formed by a preponderance of said core and effect, air texturized, synthetic, continuous filament yarn.

23. A fabric as in claim 22 further characterized in that said other of the warp and filling yarns consists substantially entirely of false twist, continuous filament texturized yarns.

24. A fabric as in claim 23 further characterized in that said core and effect, air texturized, continuous filament yarns have a denier substantially greater than the denier of the false twist yarns.

25. A fabric as in claim 24 further characterized in that the filling yarns are core and effect, air texturized, continuous filament yarns and the warp yarns are false twist texturized yarns.

26. A fabric as in claim 25 further characterized in that
both surfaces of said fabric are formed by a preponderance of said core and effect, air texturized, synthetic, continuous filament yarn.

27. A fabric for use in reusable medical/surgical products, which are to be washed, dried and sterilized subsequent to each use,
said fabric being characterized in that
it has a "hand" which, at least, closely approximates the "hand" of cotton muslin, and
further characterized in that
the "hand" of the fabric is not substantially degraded subsequent to a substantial number of washing/drying/sterilization cycles,
said fabric being further characterized in that
it has a vapor permeability sufficient to permit effective penetration by mediums employed in sterilization processes,
said fabric being a tightly woven fabric and constructionally characterized in that
said fabric is woven with a weave pattern providing raised ribs, and
the ribs are formed by texturized, continuous filament synthetic yarns,
thereby enhancing the roughness factor of the said fabric's "hand".

28. A fabric as in claim 27 further characterized in that
the fabric is a balanced, twill weave,
the filling yarns are core and effect, air texturized, continuous filament yarns, and
the warp yarns are false twist, texturized, continuous filament, synthetic yarns.

29. A fabric as in claim 28 further characterized in that the fabric is a two by two twill weave.

30. A fabric as in claim 28
further characterized in that
the fabric weave is a broken twill, herringbone weave.

31. A fabric as in claim 29
further characterized in that
the fabric weave is a broken twill, herringbone weave.

32. A medical/surgical product comprising a fabric as defined in claim 1.

33. A medical/surgical product comprising a fabric as defined in claim 8.

34. A medical/surgical product comprising a fabric as defined in claim 12.

35. A medical/surgical product comprising a fabric as defined in claim 16.

36. A medical/surgical product comprising a fabric as defined in claim 22.

37. A medical/surgical product comprising a fabric as defined in claim 27.

38. A medical/surgical product comprising a fabric as defined in claim 31.

39. A fabric for use in reusable medical/surgical products, which are to be washed, dried and sterilized subsequent to each use,
said fabric being characterized in that
it has a "hand" which approximates the "hand" of cotton muslin, and
further characterized in that
the "hand" of the fabric is not substantially degraded subsequent to a substantial number of washing/drying/sterilization cycles,
said fabric being further characterized in that
it has a vapor permeability sufficient to permit effective penetration by mediums employed in sterilization processes, and
additionally characterized that, when cut, the fabric has a minimal tendency to ravel,
said fabric being a tightly woven fabric,
constructionally characterized in that
it is formed by a set of warp yarns and a set of filling yarns, and one set of yarns comprise synthetic, continuous, multi-filament, texturized yarns forming floats which define a preponderance of at least one surface of the fabric,
and further characterized in that
the yarns are woven in a pattern which includes both floats and plain woven portions.

40. A fabric as in claim 39
further characterized in that
the fabric weave comprises a twill weave, the floats of which form diagonal ribs, and
plain woven portions disposed between each pair of adjacent ribs.

41. A fabric as in claim 40
further characterized in that
the rib forming floats of the twill weave are formed by air texturized, core and affect, filling yarns, and
each plain woven portion comprises 1 to 4 "1/1 repeats".

42. A fabric as in claim 41
further characterized in that
the fabric has a repeated weaving pattern of "2/2.1/1.1/1".

43. A fabric as in claim 42
further characterized in that
the warp and filling yarns are polyester yarns,
the filling yarns are a two ply, core and effect, air texturized, continuous filament yarn,
the warp yarns are a false twist, texturized yarns,
the bulked denier of the filling yarns is between approximately 100 and 300,
the bulked denier of the warp yarns is between approximately 50 and 150,
the fabric has between approximately 100 and 200 ends per inch and between approximately 80 and 120 picks per inch, and
the weight of the weight of the yarn content of the fabric is between approximately 2 ounces and 10 ounces per square yard.

44. A fabric as in claim 40
further characterized in that
the twill weave is a broken twill, herringbone weave, the floats of which form zigzag ribs angled first in one direction and then in an opposite direction, and
plain woven portions disposed between each adjacent pair of adjacent, zigzagged ribs.

45. A fabric as in claim 44
further characterized in that
the rib forming floats of the twill weave are formed by air texturized, core and affect, filling yarns, and
each plain woven portion comprises 1 to 4 "1/1 repeats".

46. A fabric as in claim 45
further characterized in that
the fabric has a repeated weaving pattern of "2/2.1/1.1/1 RH.2/2.1/1.1/1 LH".

47. A fabric as in claim 46
further characterized in that
the warp and filling yarns are polyester yarns, the filling yarns are a two ply, core and effect, air texturized, continuous filament yarn, the warp yarns are a false twist texturized yarns, the bulked denier of the filling yarns is between approximately 100 and 300, the bulked denier of the warp yarns is between approximately 50 and 150, the fabric has between approximately 100 and 200 ends per inch and between approximately 80 and 120 picks per inch, and the weight of the weight of the yarn content of the fabric is between approximately 2 ounces and 10 ounces per square yard.

48. A medical/surgical product comprising a fabric as defined in claim 39.

49. A fabric as in claim 1 further characterized in that the fabric has a Suter rating of at least approximately 25, a spray rating of at least about 90 and an air permeability of at least about 8 cfm at 0.5 inch of water head.

50. A fabric as in claim 26 further characterized in that the fabric has a Suter rating of at least approximately 25, a spray rating of at least about 90 and an air permeability of at least about 8 cfm at 0.5 inch of water head.

* * * * *